(12) United States Patent
Schroeder et al.

(10) Patent No.: US 6,331,646 B1
(45) Date of Patent: Dec. 18, 2001

(54) AMORPHOUS N-[N-(3,3-DIMETHYLBUTYL)-L-α-ASPARTYL]-L-PHENYLALANINE 1-METHYL ESTER

(75) Inventors: Steve A. Schroeder, Belvidere; Run Wang, Gurnee, both of IL (US)

(73) Assignee: The NutraSweet Co., Chicago, IL (US)

( * ) Notice: Subject to any disclaimer, the term of this patent is extended or adjusted under 35 U.S.C. 154(b) by 0 days.

(21) Appl. No.: 09/442,988

(22) Filed: Nov. 19, 1999

Related U.S. Application Data

(60) Provisional application No. 60/109,391, filed on Nov. 20, 1998.

(51) Int. Cl.[7] ................................................. C07C 229/24
(52) U.S. Cl. ................................................ 560/40; 560/41
(58) Field of Search ........................................ 560/40, 41

(56) References Cited

U.S. PATENT DOCUMENTS

| | | | |
|---|---|---|---|
| 5,480,668 | 1/1996 | Nofre et al. ........................ | 426/548 |
| 5,510,508 | * 4/1996 | Claude et al. . | |
| 5,728,862 | 3/1998 | Prakash ................................ | 560/40 |

OTHER PUBLICATIONS

D.J. Wink et al., "Neotame, an Alkylated Dipeptide and High Intensity Sweetener," C55 *Acta Cryst.* 1365–1368 (1999).

* cited by examiner

*Primary Examiner*—Gary Geist
*Assistant Examiner*—Leigh C. Maier
(74) *Attorney, Agent, or Firm*—Fitzpatrick, Cella, Harper & Scinto

(57) ABSTRACT

A novel amorphous N-[N-(3,3-dimethylbutyl)-L-α-aspartyl]-L-phenylalanine 1-methyl ester compound is disclosed. Also disclosed are processes for preparing the compound. The novel compound has improved solubility and dissolution properties compared to the known monohydrate.

32 Claims, 4 Drawing Sheets

AMORPHOUS N-[N-(3,3-DIMETHYLBUTYL)-L-α-ASPARTYL]-L-PHENYLALANINE 1-METHYL ESTER

This application claims the benefit of U.S. Provisional Patent Application No. 60/109,391, filed Nov. 20, 1998.

BACKGROUND OF THE INVENTION

1. Field of the Invention

This invention is related to amorphous N-[N-(3,3-dimethylbutyl)-L-α-aspartyl]-L-phenylalanine 1-methyl ester (neotame). The invention is also directed to processes of preparing amorphous neotame, such as by melt-processing. Amorphous neotame is advantageous compared to other forms of neotame because of improved solubility and dissolution.

2. Related Background Art

Neotame is a known sweetener that has a sweetening potency that is about 40 times that of aspartame and about 8,000 times that of sucrose. N-[N-(3,3-dimethylbutyl)-L-α-aspartyl]-L-phenylalanine 1-methyl ester may be prepared from aspartame as described in U.S. Pat. Nos. 5,480,668, 5,510,508 and 5,728,862, all of which are incorporated by reference herein.

As described in those patents, neotame is crystallized from a methanol/water solution to provide neotame monohydrate, i.e., one molecule of water and one molecule of neotame. The crystal structure of neotame monohydrate is known. See e.g., "Neotame, an alkylated dipeptide and high intensity sweetener", Acta Cryst. (1999) C55, 1365–1368.

SUMMARY OF THE INVENTION

This invention relates to amorphous N-[N-(3,3-dimethylbutyl)-L-α-aspartyl]-L-phenylalanine 1-methyl ester (amorphous neotame). As used herein, the term amorphous is defined as a non-crystalline solid material. In one embodiment of this invention the amorphous neotame may be prepared by the process comprising the steps of (i) melting N-[N-(3,3-dimethylbutyl)-L-α-aspartyl]-L-phenylalanine 1-methyl ester and (ii) cooling the melt to produce a melt-processed neotame, i.e., amorphous neotame.

Another embodiment of this invention is directed to the process of preparing amorphous neotame by milling, most preferably by ball milling. Yet another embodiment of this invention is directed to the process of preparing amorphous neotame by dissolving neotame in an organic solvent and recovering amorphous neotame from the solvent. Generally, the amorphous neotame is recovered by evaporation of the solvent or separating the amorphous neotame from the solvent by, for example, filtration.

Preferably, the neotame that is used to prepare amorphous neotame by the techniques described above can be any hydrated form, such as a monohydrate (about 4.0% to 4.5% $H_2O$), an intermediate hydrate (about 1.0% to 4.0% $H_2O$) or an anhydrate (less than about 1.0% $H_2O$) or combinations thereof. In addition, it is also possible for the neotame to contain excess water, i.e., greater than about 4.5% $H_2O$. Most preferably the neotame is the monohydrate form. The amorphous neotame of this invention is characterized by an x-ray diffraction pattern as depicted in FIG. 1.

DETAILED DESCRIPTION OF THE DRAWING

DETAILED DESCRIPTION OF THE INVENTION

Figure 1:
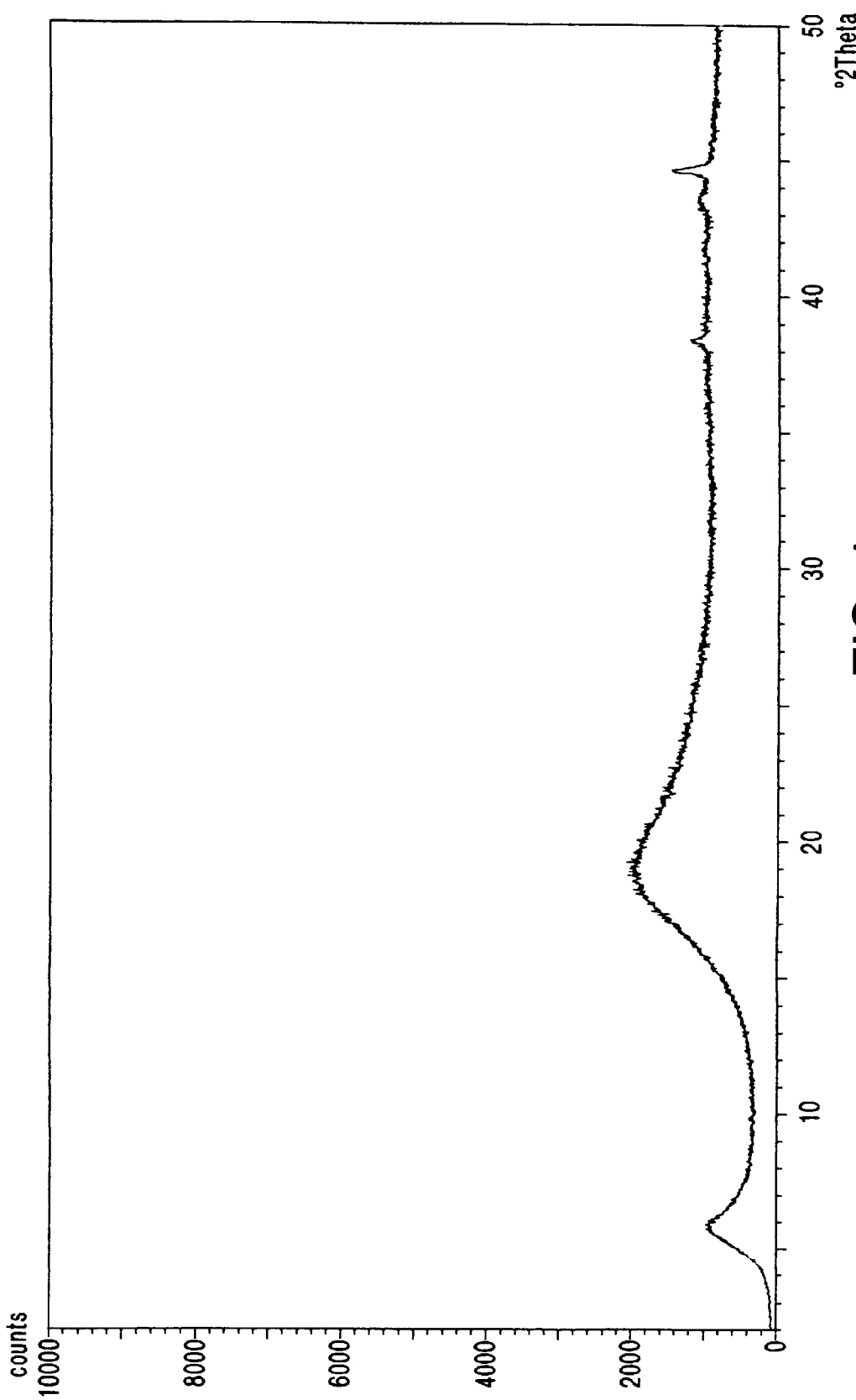
FIG. 1 illustrates the x-ray diffraction pattern of the amorphous neotame of this invention.
Figure 2:
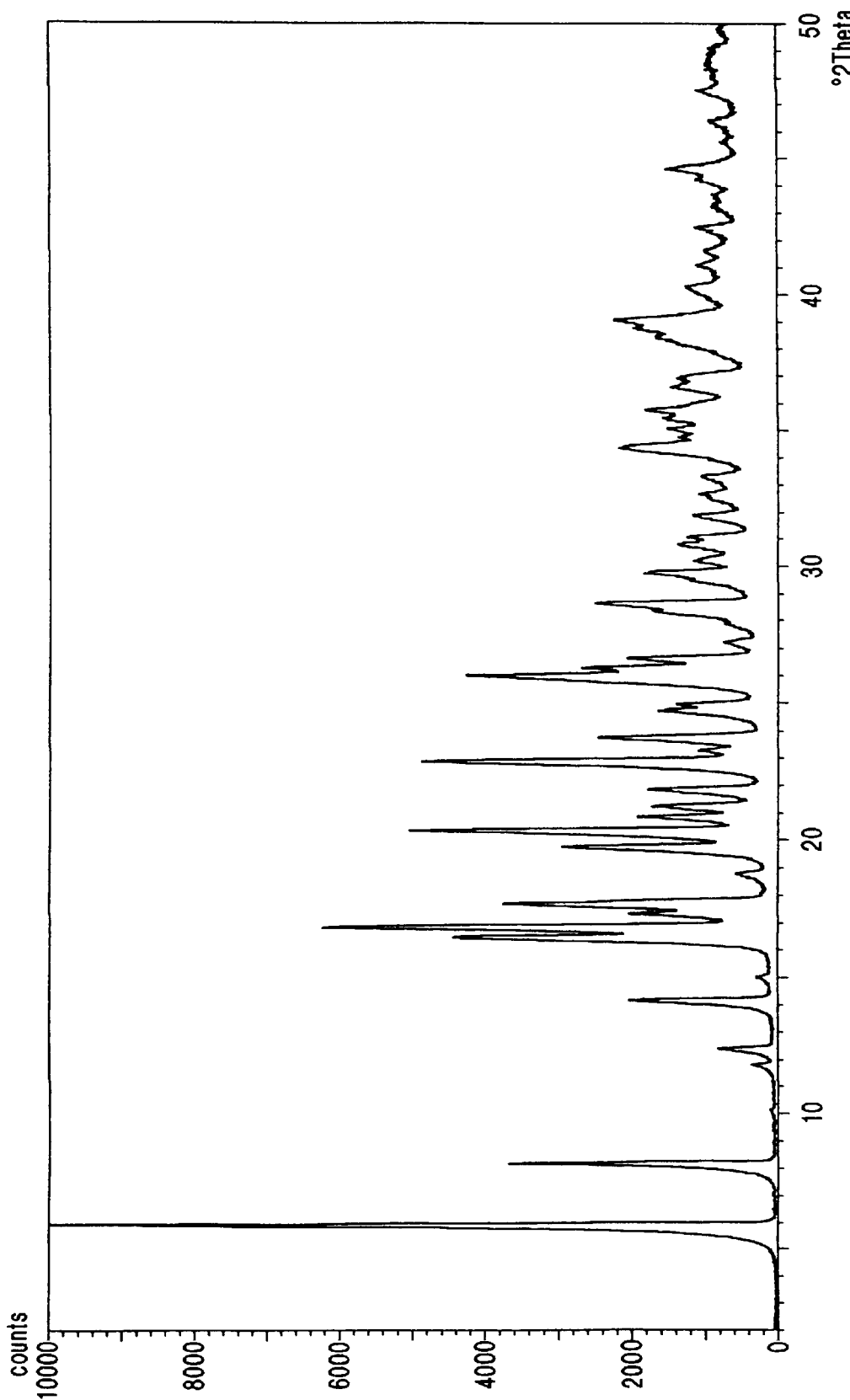
FIG. 2 illustrates the x-ray diffraction pattern of neotame monohydrate.

This invention is directed to amorphous neotame. Most preferably the amorphous neotame is substantially pure amorphous neotame.

The novel form of amorphous neotame (amorphous N-[N-(3,3-dimethylbutyl)-L-α-aspartyl]-L-phenylalanine 1-methyl ester) may be produced by melting non-amorphous neotame, followed by solidifying the melt to produce solid material. This novel form has advantages of higher solubility and a reduced rate of dissolution compared to that of the monohydrate form of neotame in a variety of solvents commonly used in the food industry. A reduced rate of dissolution may be preferred in processing of food formulations such as chewing gum and baking applications.

The amorphous neotame of this invention has a high degree of sweetness. The amorphous neotame is believed to have a sweetening potency of around 40 times that of aspartame.

The amorphous neotame of this invention can exist under normal storage and processing conditions and can be used in typical and conventional food applications. One particular feature concerning the use of any food ingredient is its solubility (defined as the amount of material dissolved at a particular temperature at equilibrium conditions) and dissolution (defined as the rate of which the material dissolves) properties in various food compositions. For end-use commercial liquid systems such as beverages, dissolution of neotame is more important than solubility due to neotame's high potency level. For traditional dry systems, or low-moisture food systems such as chewing gum, baking, dairy, and pharmaceutical applications, both dissolution and solubility of neotame within the blend composition will be important considerations.

Because of its extremely high potency compared to other commercially available high intensity sweeteners, a liquid delivery form is particularly advantageous. Therefore the solubility of neotame will also be an important consideration in any liquid delivery system containing neotame. Preferably, the greater the solubility in a particular solvent the less solvent used for any particular application, thus resulting in a potential cost savings of ingredients. In addition, greater solubility in any particular solvent may result in an added benefit of increasing the stability of neotame, since stability has always been a concern with dipeptide based sweetener ingredients. Slower dissolution of dipeptide sweeteners such as neotame is advantageous in the processing of many low-moisture food formulations such as those of bakery, dairy, and chewing gum because the stability of the dipeptide sweetener can be increased. Degradation by interaction with other components in the food system is enhanced once the sweetener has sufficiently dissolved in the formulation. Thus, it is believed that a slower rate of dissolution of amorphous neotame in these compositions will result in an increase of stability of neotame compared to that provided by non-amorphous neotame. The amorphous neotame of this invention provides improved solubility and dissolution compared to the known monohydrate form and thus may be highly advantageous in food and beverage applications.

Another embodiment of this invention is directed to a process of producing amorphous neotame using a melt-processed technique. The melting temperature required in the process of this invention will differ depending on the form of starting neotame. This melting temperature can be readily determined by simple observation. For example, neotame monohydrate is heated above its melting point of about 82.2° C. to form a liquid melt. Generally, the melt temperature must be at least about 75° C. The typical temperature range for melting the monohydrate is from about 82° C. to about 200° C. The preferred range is about 85° C. to about 120° C. and the most preferred range is about 87° C. to about 95° C. The melting point of anhydrous neotame is about 92° C. In this case, the typical temperature range for melting the anhydrous neotame is from about 92° C. to about 200° C. The preferred range is about 95° C. to about 125° C. and the most preferred range is from about 97° C. to about 105° C. The melting point temperatures described above are average melting temperatures at atmospheric pressure and will vary depending on the processing pressure.

The amount of time to produce the melt, once the melting temperature has been reached will depend on the amount of neotame used. The amount of time used for the melting process should be enough to ensure the melting of all of the neotame present. Once the neotame has all melted, it is then allowed to cool to solidify. There are no specific limits as to the temperature of cooling or rate of cooling after the melting of neotame is completed.

The amorphous neotame obtained from the melt-processing described above is a hard brittle glassy-like solid. The amorphous neotame of this invention is characterized by the x-ray diffraction pattern of FIG. 1. There is no specific limitation regarding further processing of the amorphous neotame, as the amorphous neotame can be processed to achieve a desirable particle size by granulating or other means to form free-flowing particles.

Another embodiment of this invention is directed to a method of producing amorphous neotame by milling non-amorphous neotame. The step of milling is a mechanical process that, without being bound to theory, is believed to produce localized areas of energy that converts crystalline forms of neotame to the amorphous form. Exemplary milling techniques useful in the method of this invention include ball milling or air jet milling. Ball milling is the most preferred technique. Such milling techniques are well known to those of ordinary skill in the art.

The starting neotame used in the milling process of this invention may be the same as the forms of neotame used in the melt processed technique. The non-amorphous neotame is milled for a period of time and at a speed effective to form amorphous neotame. These parameters can be readily determined by those of ordinary skill in the art. Typical milling time periods may range from about 15 minutes to about 2 hours, although other time periods may be employed as desired. The resulting amorphous neotame derived from milling is a powder and is characterized by the x-ray diffraction pattern shown in FIG. 1.

Yet another embodiment of this invention includes a method to prepare amorphous neotame comprising the steps of mixing non-amorphous neotame with an organic solvent substantially free of water and recovering amorphous neotame from the organic solvent. The starting neotame used in this organic solvent process may take the same forms as the neotame used in the melt-processed technique. As used herein, organic solvents include one or more organic solvents which are substantially free of water, i.e., having less than about 3% water, more preferably less than 1% water. Useful organic solvents include, for example, methanol, toluene, ethyl acetate, hexane, ethanol, acetone, dioxane, tetrahydrofuran and mixtures thereof. Organic solvents useful in this invention may be purchased substantially free of water or dried using known techniques. Generally about 0.05 to about 75 percent by weight starting neotame is added to the organic solvent system. The amount of neotame mixed with the organic solvent will of course depend on its solubility in the solvent and the temperature. Generally, the process is conducted at room temperature, although other higher or lower temperatures may be used as desired depending on the solubility of neotame. It should be recognized, however, that while it is preferable to completely dissolve the non-amorphous neotame in the organic solvent, the process may also be useful even if some of the non-amorphous neotame does not dissolve. The neotame is left in the solvent for a time sufficient to convert the non-amorphous neotame to amorphous neotame. Such time periods may range from several minutes to several days or more. The appropriate time period and temperatures of the process can be readily determined by one of ordinary skill in the art.

The amorphous neotame may be recovered from the organic solvent by standard or conventional techniques. For example, by solvent evaporation followed by filtration. It may be possible to precipitate the dissolved mixture by addition of an appropriate organic solvent followed by filtration. The amorphous mixture prepared by this process of the invention is a powder and is characterized by the x-ray diffraction pattern illustrated in FIG. 1.

The examples which follow are intended as illustrations of preferred embodiment of the invention and no limitation of the invention is implied.

EXAMPLE 1

25 grams of neotame was spread out equally on six containers and heated slowly past its melting point of about 82° C. until a temperature of about 92° C. was reached. The rate of heating after the initial melting of neotame was observed to be about 1° C./minute. Once 92° C. was reached, all of the neotame was melted. The containers containing the neotame were removed from the oven and allowed to cool to room temperature, about 23° C. The neotame was removed from the containers, and ground to a crystalline powder with a mortar and pestle. The x-ray diffraction pattern of the resulting amorphous neotame is illustrated in FIG. 1. Rates of dissolution and solubility measurements were then determined in several different solvent systems (deionized water; 0.1M phosphate (pH3) in water; 10:90 Ethanol (EtOH):$H_2O$; and 50:50 Ethyl Acetate (EtAc):Hexane) and compared to the conventional form of the neotame monohydrate. The solubility results are set forth below:

| SOLUBILITY (grams of neotame/100 grams solvent) | | | | |
|---|---|---|---|---|
| | Solvents | | | |
| | Water | 0.1 M Phosphate pH3 | 10:90 EtOH:H₂O | 50:50 EtAc:Hexane |
| Neotame Monohydrate | 1.28 | 1.35 | 1.55 | 1.29 |
| Example 1 | 1.35 | 1.49 | 1.57 | 3.07 |

Figure 3:
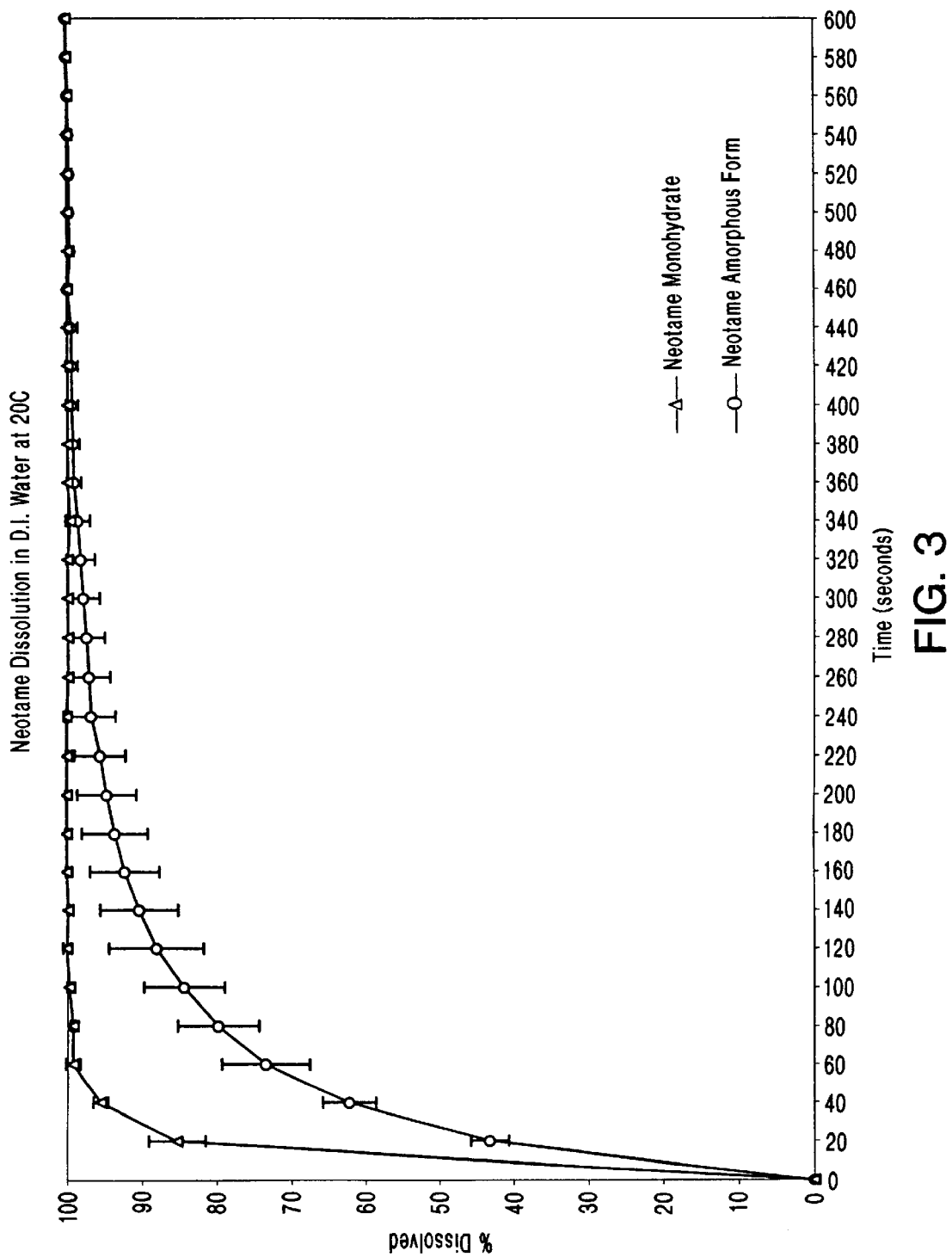
FIG. 3 illustrates a graphical representation of the dissolution rate of amorphous neotame and neotame monohydrate in deionized water at 20° C.
Figure 4:
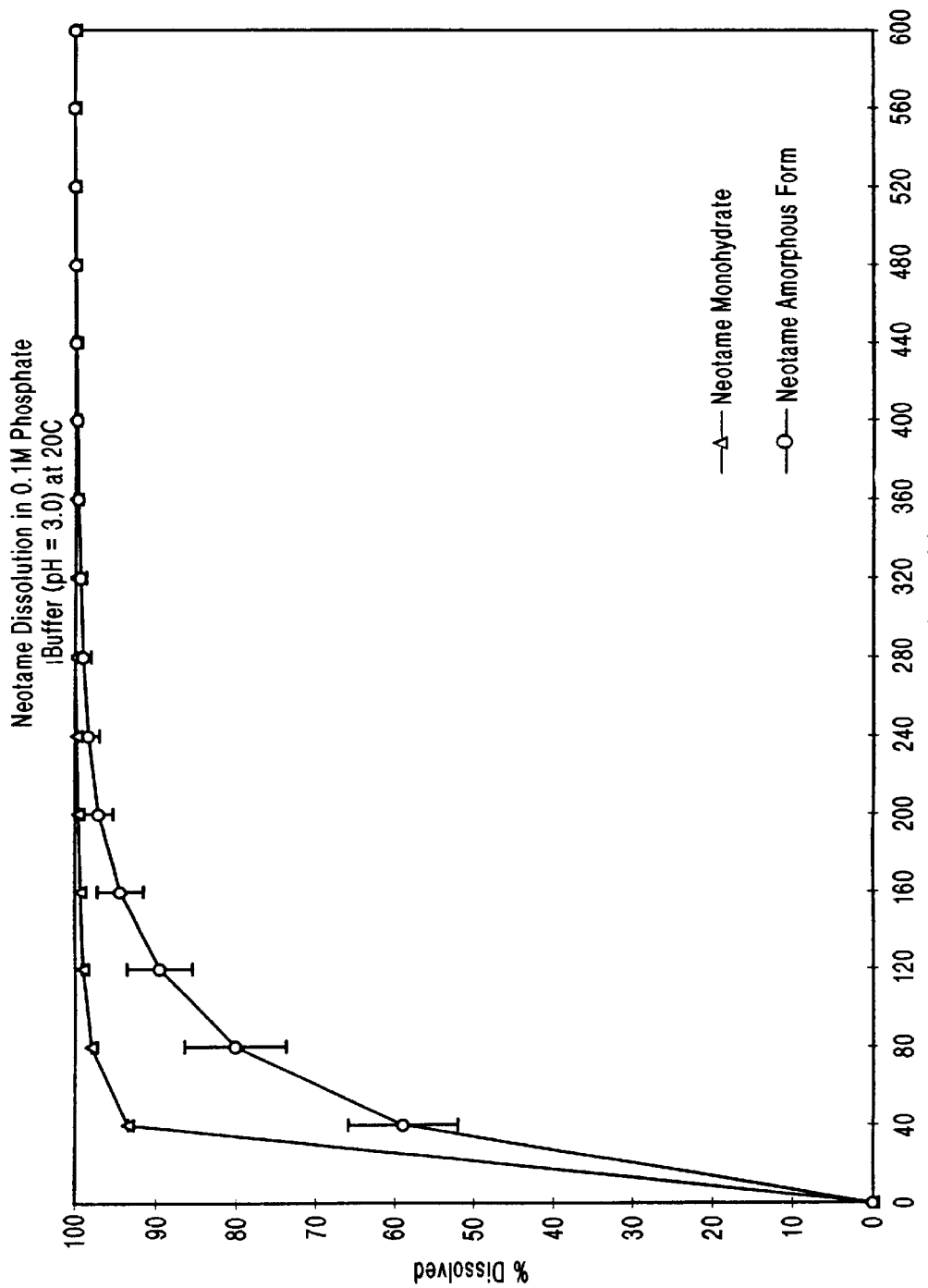
FIG. 4 illustrates a graphical representation of the dissolution rate of amorphous neotame and neotame monohydrate in 0.1 M phosphate buffer at 20° C.

FIG. 3 illustrates a comparison of the dissolution of the amorphous neotame of Example 1 with neotame monohydrate in deionized water at 20° C. FIG. 4 illustrates a similar comparison in 0.1 M phosphate buffer.

EXAMPLE 2

Neotame monohydrate (1.5 grams) was subjected to milling in a ball mill (Glen Creston, London, England). After 6 hours of milling the neotame monohydrate was nearly entirely converted to anhydrous neotame. The resulting amorphous neotame is characterized by an x-ray diffraction pattern such as illustrated in FIG. 1.

EXAMPLE 3

Neotame monohydrate (9.2 grams) was added to methanol (8 mls). The mixture was allowed to stand for 3 days, after which the mixture was filtered by vacuum filtration and the solid recovered. The resulting solid was amorphous neotame characterized by an x-ray diffraction pattern such as illustrated in FIG. 1.

EXAMPLE 4

Neotame monohydrate (9 grams) was mixed with toluene (20 mls). The toluene was evaporated in a vacuum oven at 50° C. The resulting product was amorphous neotame characterized by an x-ray diffraction pattern such as illustrated in FIG. 1.

EXAMPLE 5

Neotame monohydrate (3.5 grams) was mixed with 50:50 ethyl acetate/hexane (130 grams). The solvent was evaporated in a vacuum oven at 50° C. The resulting product was amorphous neotame characterized by an x-ray diffraction pattern such as illustrate in FIG. 1.

Other variations and modifications of this invention will be obvious to those skilled in the art. This invention is not limited except as set forth in the claims.

What is claimed is:

1. An non-crystalline amorphous N-[N-(3,3-dimethylbutyl)-L-α-aspartyl]-L-phenylalanine 1-methyl ester.

2. The non-crystalline amorphous N-[N-3,3-dimethylbutyl)-L-α-aspartyl]-L-phenylalanine 1-methyl ester according to claim 1, characterized by the x-ray diffraction pattern of FIG. 1.

3. The non-crystalline amorphous N-[N-(3,3-dimethylbutyl)-L-α-aspartyl]-L-phenylalanine 1-methyl ester according to claim 1, wherein said amorphous N-[N-(3,3-dimethylbutyl)-L-α-aspartyl]-L-phenylalanine is substantially pure.

4. An amorphous N-[N-(3,3-dimethylbutyl)-L-α-aspartyl]-L-phenylalanine 1-methyl ester compound prepared by the process comprising the steps of (i) melting N-[N-(3,3-dimethylbutyl)-L-α-aspartyl]-L-phenylalanine 1-methyl ester and (ii) cooling the melt to produce the amorphous N-[N-(3,3-dimethylbutyl)-L-α-aspartyl]-L-phenylalanine 1-methyl ester compound.

5. The compound according to claim 4, wherein the N-[N-(3,3-dimethylbutyl)-L-α-aspartyl]-L-phenylalanine 1-methyl ester that is melted in step (i) is an anhydrous or monohydrate form.

6. The compound according to claim 4, wherein the N-[N-(3,3-dimethylbutyl)-L-α-aspartyl]-L-phenylalanine 1-methyl ester that is melted in step (i) is a monohydrate form.

7. The compound according to claim 6, wherein step (i) comprises heating the N-[N-(3,3-dimethylbutyl)-L-α-aspartyl]-L-phenylalanine 1-methyl ester to a temperature of at least about 82° C.

8. The compound according to claim 7, wherein said temperature is about 82° C. to about 200° C.

9. The compound according to claim 4, wherein the N-[N-(3,3-dimethylbutyl)-L-α-aspartyl]-L-phenylalanine 1-methyl ester that is melted in step (i) is an anhydrous form.

10. The compound according to claim 9, wherein step (i) comprises heating the N-[N-(3,3-dimethylbutyl)-L-α-aspartyl]-L-phenylalanine 1-methyl ester to a temperature of at least about 92° C.

11. The compound according to claim 10, wherein said temperature is about 92° C. to about 200° C.

12. A process for preparing non-crystalline amorphous N-[N-(3,3-dimethylbutyl)-L-α-aspartyl]-L-phenylalanine 1-methyl ester compound comprising the steps of (i) melting N-[N-(3,3-dimethylbutyl)-L-α-aspartyl]-L-phenylalanine 1-methyl ester and (ii) cooling the melt to produce the amorphous N-[N-(3,3-dimethylbutyl)-L-α-aspartyl]-L-phenylalanine 1-methyl ester compound.

13. The process according to claim 12, wherein the N-[N-(3,3-dimethylbutyl)-L-α-aspartyl]-L-phenylalanine 1-methyl ester that is melted in step (i) is an anhydrous or monohydrate form.

14. The process according to claim 12, wherein the N-[N-(3,3-dimethylbutyl)-L-α-aspartyl]-L-phenylalanine 1-methyl ester that is melted in step (i) is a monohydrate form.

15. The process according to claim 14, wherein step (i) comprises heating the N-[N-(3,3-dimethylbutyl)-L-α-aspartyl]-L-phenylalanine 1-methyl ester to a temperature of at least about 82° C.

16. The process according to claim 15, wherein said temperature is about 82° C. to about 200° C.

17. The process according to claim 12, wherein the N-[N-(3,3-dimethylbutyl)-L-α-aspartyl]-L-phenylalanine 1-methyl ester that is melted in step (i) is an anhydrous form.

18. The process according to claim 17, wherein step (i) comprises heating the N-[N-(3,3-dimethylbutyl)-L-α-aspartyl]-L-phenylalanine 1-methyl ester to a temperature of at least about 92° C.

19. The process according to claim 18, wherein said temperature is about 92° C. to about 200° C.

20. An non-crystalline amorphous N-[N-(3,3-dimethylbutyl)-L-α-aspartyl]-L-phenylalanine 1-methyl ester compound prepared by the process comprising the step of milling N-[N-(3,3-dimethylbutyl)-L-α-aspartyl]-L-phenylalanine 1-methyl ester for a time sufficient to form said amorphous N-[N-(3,3-dimethylbutyl)-L-α-aspartyl]-L-phenylalanine 1-methyl ester.

21. The compound according to claim 20, wherein said step of milling comprises ball milling.

22. A process for preparing amorphous N-[N-(3,3-dimethylbutyl)-L-α-aspartyl]-L-phenylalanine 1-methyl ester compound comprising the step of milling N-[N-(3,3-dimethylbutyl)-L-α-aspartyl]-L-phenylalanine 1-methyl ester for a time sufficient to form said amorphous N-[N-(3,3-dimethylbutyl)-L-α-aspartyl]-L-phenylalanine 1-methyl ester.

23. The process according to claim 22, wherein said step of milling comprises ball milling.

24. The process according to claim 23, wherein said step of ball milling is performed for a time in a range of about 15 minutes to about 2 hours.

25. An non-crystalline amorphous N-[N-(3,3,-dimethylbutyl-L-α-aspartyl]-L-phenylalanine 1-methyl ester compound prepared by the process comprising the steps of (i) mixing N-[N-(3,3-dimethylbutyl)-L-α-aspartyl]-L-phenylalanine 1-methyl ester with an organic solvent substantially free of water and (ii) recovering said amorphous N-[N-(3,3-dimethylbutyl)-L-α-aspartyl]-L-phenylalanine 1-methyl ester from said mixture.

26. The compound according to claim 25, wherein said organic solvent is selected from the group consisting of methanol, toluene, ethyl acetate, hexane, ethanol, acetone, dioxane, tetrahydrofuran and mixtures thereof.

27. The compound according to claim 25, wherein the weight percent of N-[N-(3,3-dimethylbutyl)-L-α-aspartyl]-L-phenylalanine 1-methyl ester mixed with said organic solvent is in a range of about 0.05% to about 75% by weight of the mixture.

28. The compound according to claim 25, wherein the step of recovery comprises at least one of filtration and evaporation.

29. A process for forming an non-crystalline amorphous N-[N-(3,3,-dimethylbutyl)-L-α-aspartyl]-L-phenylalanine 1-methyl ester compound comprising the steps of (i) mixing N-[N-(3,3-dimethylbutyl)-L-α-aspartyl]-L-phenylalanine 1-methyl ester with an organic solvent substantially free of water and (ii) recovering said amorphous N-[N-(3,3-dimethylbutyl)-L-α-aspartyl]-L-phenylalanine 1-methyl ester from said mixture.

30. The process according to claim 29, wherein said organic solvent is selected from the group consisting of methanol, toluene, ethyl acetate, hexane, ethanol, acetone, dioxane, tetrahydrofuran and mixtures thereof.

31. The process according to claim 29, wherein the weight percent of N-[N-(3,3-dimethylbutyl)-L-α-aspartyl]-L-phenylalanine 1-methyl ester mixed with said organic solvent is in a range of about 0.05% to about 75% by weight of the mixture.

32. The process according to claim 29, wherein the step of recovery comprises at least one of filtration and evaporation.

* * * * *

UNITED STATES PATENT AND TRADEMARK OFFICE
CERTIFICATE OF CORRECTION

PATENT NO.   : 6,331,646 B1
DATED        : December 18, 2001
INVENTOR(S)  : Schroeder, Stephen et al.

It is certified that error appears in the above-identified patent and that said Letters Patent is hereby corrected as shown below:

Column 5,
Line 48, "illustrate" should read -- illustrated --; and
Line 54, "An" should read -- A --.

Column 6,
Line 59, "An" should read -- A --.

Column 7,
Line 13, "An" should read -- A --.

Column 8
Line 6, "an" should read -- a --.

Signed and Sealed this

Thirtieth Day of April, 2002

Attest:

Attesting Officer

JAMES E. ROGAN
Director of the United States Patent and Trademark Office